United States Patent
Liska (10) Patent No.: US 10,596,351 B2
(45) Date of Patent: Mar. 24, 2020

(54) SELF-SEALING CATHETER VALVE

(71) Applicant: TRADINCO AB, Stockholm (SE)

(72) Inventor: Jan Liska, Stockholm (SE)

(73) Assignee: TRAINCO AB, Stockholm (SE)

( * ) Notice: Subject to any disclaimer, the term of this patent is extended or adjusted under 35 U.S.C. 154(b) by 0 days.

(21) Appl. No.: 15/527,571

(22) PCT Filed: Dec. 3, 2015

(86) PCT No.: PCT/EP2015/078570
§ 371 (c)(1),
(2) Date: May 17, 2017

(87) PCT Pub. No.: WO2016/087606
PCT Pub. Date: Jun. 9, 2016

(65) Prior Publication Data
US 2017/0326341 A1 Nov. 16, 2017

(30) Foreign Application Priority Data

Dec. 3, 2014 (EP) ................................. 14196068

(51) Int. Cl.
*A61M 5/00* (2006.01)
*A61M 25/06* (2006.01)
(Continued)

(52) U.S. Cl.
CPC .... *A61M 25/0606* (2013.01); *A61M 25/0097* (2013.01); *A61M 25/0662* (2013.01);
(Continued)

(58) Field of Classification Search
CPC .......... A61M 25/0097; A61M 25/0606; A61M 39/0693; A61M 39/24; A61M 2039/062; A61M 2039/2493; A61M 2039/242
See application file for complete search history.

(56) References Cited

U.S. PATENT DOCUMENTS 3,889,675 A 6/1975 Stewart
4,436,519 A 3/1984 O'Neill
(Continued)

FOREIGN PATENT DOCUMENTS

EP 0 257 880 A1 3/1988
WO 2009/016184 A1 2/2009
WO 2011/073969 A1 6/2011

OTHER PUBLICATIONS

International Search Report and Written Opinion, Appl. No. PCT/EP2015/078570, dated Feb. 12, 2016.
(Continued)

*Primary Examiner* — Elmer M Chao
(74) *Attorney, Agent, or Firm* — Winston & Strawn LLP (57) ABSTRACT

A self-sealing catheter valve that includes a flexible tubular part having a distal opening and an opposite proximal opening, and a proximal valve part. The proximal valve part has a curved self-sealing flexible diaphragm disposed inside the flexible tubular part and has a base perimeter united with a circumferential wall of the flexible tubular part. The curved self-sealing flexible diaphragm has a concave surface facing towards the proximal opening, and a convex surface facing towards the distal opening, and a flexible diaphragm wall of the curved self-sealing flexible diaphragm has a traverse slit. The self-sealing catheter valve provides an efficient self-closing mechanism for a peripheral catheter assembly and constitutes an efficient barrier against potential contagious spread from the patient to the surrounding environment by blood born disease e.g. HIV, hepatitis and Ebola viruses.

15 Claims, 5 Drawing Sheets

(51) Int. Cl.
  *A61M 39/04* (2006.01)
  *A61M 39/06* (2006.01)
  *A61M 25/00* (2006.01)
  *A61M 39/22* (2006.01)
  *A61M 39/00* (2006.01)

(52) U.S. Cl.
  CPC .......... *A61M 39/04* (2013.01); *A61M 39/045* (2013.01); *A61M 39/06* (2013.01); *A61M 39/0606* (2013.01); *A61M 39/228* (2013.01); *A61M 2039/0036* (2013.01); *A61M 2039/0072* (2013.01); *A61M 2039/064* (2013.01)

(56) References Cited

U.S. PATENT DOCUMENTS

| | | | |
|---|---|---|---|
| 5,269,763 A | 12/1993 | Boehmer et al. | |
| 5,334,159 A * | 8/1994 | Turkel | A61B 17/3496 604/158 |
| 5,456,284 A | 10/1995 | Ryan et al. | |
| 5,533,708 A * | 7/1996 | Atkinson | A61M 39/045 251/149.1 |
| 6,039,718 A | 3/2000 | Niedospial, Jr. | |
| 2002/0179527 A1* | 12/2002 | Yao | C09K 3/1021 210/634 |
| 2008/0058720 A1* | 3/2008 | Spohn | A61M 5/007 604/140 |
| 2013/0090607 A1 | 4/2013 | McKinnon et al. | |

OTHER PUBLICATIONS

International Preliminary Report on Patentability, Chapter II, Appl. No. PCT/EP2015/078570, dated Dec. 1, 2016.
European Search Report, Appl. No. 14196068.2, dated Apr. 22, 2015.

* cited by examiner

SELF-SEALING CATHETER VALVE

This application is a 371 filing of International Patent Application PCT/EP2015/078570 filed Dec. 3, 2015, which claims the benefit of European application no. 14196068.2 filed Dec. 3, 2014.

BACKGROUND

The present invention relates to a self-sealing catheter valve including
- a flexible tubular part having a distal opening and an opposite proximal opening, and
- a proximal valve part that has a curved self-sealing flexible diaphragm disposed inside the flexible tubular part and has a base perimeter united with a circumferential wall of the flexible tubular part,
- the curved self-sealing flexible diaphragm has a concave surface facing towards the proximal opening and a convex surface facing towards the distal opening, and
- 1a flexible diaphragm wall of the curved self-sealing flexible diaphragm has a traverse slit.

The conventional peripheral catheter which is used all over the world has a tip for insertion into the blood vessel, wings for manual handling and securing the catheter with adhesives, a valve to allow injection of drugs with a syringe, and an end which allows connection to an intravenous infusion line or allows capping in between uses. A needle serves as a "guidewire" for inserting the catheter into the vein.

US patent application no. 2013/090607 discloses an alternative intravenous catheter with a catheter adapter that includes a valve. The valve serve the dual function of a selectively sealing both an infusion port and the internal lumen of the catheter adapter. The valve is a duckbill valve, which includes two inwardly oriented flaps, which are biased together toward a central position, forming a slit. These flaps can extend from a tube portion of the valve inwardly and distally to be pushed together to close the valve in response to a fluid flow in a proximal direction towards the distal end of the catheter adapter. Additionally, the two inwardly oriented flaps can be pushed apart to open a gap between these flaps in response to a fluid flow in a distal direction. The duck bill design with straight flaps that delimit the traverse slit are not compatible with opening and closing of concave and convex membrane surfaces.

U.S. Pat. No. 5,456,284 discloses a different duckbill valve without a curved self-sealing flexible diaphragm disposed inside the flexible tubular part. This known duckbill valve features a cat-eye effect, albeit this effect is alleged reduced. Even the smallest cat-eye effect causes undesired leakage of the valve of this known duckbill valve.

U.S. Pat. No. 3,889,675 relates to a disposable suction-irrigating instrument for delivering sterile fluid and applying suction to an operating work area. The instrument includes a valve assembly having a part of its length exposed for contact by the fingers of the operator for controlling the supply of the fluid delivered by the instrument. The valve assembly comprises a resilient tubular connector, a diaphragm integral with and mounted across the bore of the connector, and a slit in the diaphragm having sides that normally abut each other to thereby close the bore but which are spread apart and permit passage of fluid upon application and deformation of the diaphragm by pressure against the outside of the connector from the operator's fingers. Valves that require the operator to use his/her fingers from outside the valve is not part of the present invention.

U.S. Pat. No. 5,269,763 relates to a cross-slit valve. Cross-slit valves suffers from the disadvantage of having too many degrees of freedom when it come to closing the web members of adjacent lips of the cross-slit arrangement after an inserted objects has been removed. The web members of adjacent lips intersect each other along web intersection lines and each of the intersection lines extend radially inwardly in a direction from the inlet to the outlet end of the valve body thereby defining a valve without concave and convex membrane surfaces.

Applicant's International patent application no. WO 2009 016184 relates to another kind of peripheral catheter assembly having precautionary means for avoiding spillage of blood during insertion and during infusion. To that aspect applicant's peripheral catheter assembly comprises a sealing valve having a septum seal. The septum seal has deflectable septum walls, and a hollow tubular extension which protrudes towards a free end from the periphery of the septum seal and extends inside the catheter hub past the injection port towards the distal end of the catheter hub to provide a self-closable sealing member which provides the physician the freedom to leave the patient when the needle module is retracted. It has however now been realised that although the sealing valve described in WO 2009 016184 has many advantages, it's sealing properties deteriorates too fast, in particular sterilizing sometimes alters the sealing valve's sealing properties to an extent that the sealing valve may leak, e.g. during the insertion procedure.

U.S. Pat. No. 4,436,519 relates to an alternative kind of valve, namely a hemostasis valve comprising a dome-shaped diaphragm wall member with a securing flange. The dome-shaped diaphragm wall has a diaphragm slit opposite the flange. This narrow small slit can open to allow passage of an inserted catheter. Upon forcing the catheter through the diaphragm slit, a diaphragm rib compresses against an upper central passage wall of a special house fitting. Upon withdrawing the catheter from the hemostasis valve the compressed diaphragm rib expands to its original position, causing the diaphragm slit to close. The exterior face of the hemostasis valve fits tightly into an assembly of plural parts, the special house fitting, including various connectors, extra seals, caps and fasteners that when assembled keep the hemostasis valve in fixed position of use when a needle is introduced into a blood vessel via the rather deep valve chamber defined by the cavity of the dome. A male Luer coupling cannot be inserted through the slit of the dome, nor is such intended or described in U.S. Pat. No. 4,436,519.

Thus there is still a demand between physicians and medical staff for improved sealing valves for peripheral catheters that makes catheter insertion easier, safer and more reliable.

SUMMARY OF THE INVENTION

In a first aspect is provided a self-sealing catheter valve of the kind mentioned in the opening paragraph that remedies some of the disadvantages and shortcomings of the prior art catheter valves.

In a second aspect is provided a self-sealing catheter valve of the kind mentioned in the opening paragraph, which self-closes the flow path when the needle is removed after venipuncture, and opens a flow path in response to introduction of a male part in the catheter hub.

In a third aspect is provided a self-sealing catheter valve, which can be implemented in a conventional catheter hub with an injection port.

In a fourth aspect is provided a self-sealing catheter valve of the kind mentioned in the opening paragraph, which does not leak through the valve when the needle guide inside the catheter is retracted after the catheter is placed inside the blood vessel.

In a fifth aspect is provided a self-sealing catheter valve of the kind mentioned in the opening paragraph, which protect personal from blood spillage and blood born contamination from the patient.

The novel and unique whereby these and other aspects are achieved according to the present invention is the fact that
the convex surface (10) of the curved self-sealing flexible diaphragm (7) has an upright rib (16a,16b,16) extending crosswise the traverse slit (15) towards the interior surface of the circumferential wall (9) of the flexible tubular part (2).

Within the context of the present application "self-sealing flexible diaphragm" is to be understood as a flexible, fluid-tight, sealing structure. The "self-sealing flexible diaphragm" is made of a semi-flexible or flexible material, such as silicone, and the diaphragm is anchored at its periphery to another flexible member, the tubular part. The self-sealing flexible diaphragm defines a barrier between the surroundings and the blood vessel. The self-sealing flexible diaphragm is placed a distance inside the tubular part, thus the tubular part are the part of the valve in engagement with the needle hub, e.g. as described in WO 2009 016184, and/or other tubular passageway of a catheter assembly. Thus the surfaces or perimeter of the "self-sealing flexible diaphragm" itself has no direct contact with other parts of the catheter assembly other than when the over-the-needle-catheter is passed through the traverse slit in order to insert a catheter into a blood vessel.

The self-sealing flexible diaphragm is adapted to counteract pressures on the respective concave and convex surfaces, still keeping the traverse slit fluid tight closed, but also allowing more or less opening of the traverse slit when an object is pushed through this traverse slit, optionally mounted through the traverse slit on a more permanent basis, such as when a male Luer provides for infusion. So the self-sealing flexible diaphragm opens and closes the traverse slit depending on differences in pressure on opposite curved surfaces, thereby making the flexible diaphragm self-sealing. The self-sealing flexible diaphragm may e.g. be used in a catheter assembly corresponding to the catheter assembly known from WO 2009 016184. Once the needle has been retracted and the catheter left in the blood vessel blood flows back into the catheter assembly but is stopped by the convex surface of the flexible diaphragm wall of the curved self-sealing flexible diaphragm. The blood pressure of the patient puts a pressure on the convex surface of the flexible diaphragm and causes the traverse slit to close completely or to seal around the inserted object, whether such object being a catheter or a male Luer connector. A capping may be provided to the catheter hub for further precaution to prevent leakage. Due to the special convex curvature the blood pressure is too low to accidentally invert the self-sealing flexible diaphragm. In one simple embodiment the self-sealing flexible diaphragm may resemble a segmental dome-, dish- or boat-shape.

The convex surface of the curved self-sealing flexible diaphragm may have an upright rib extending crosswise the traverse slit towards the interior surface of the circumferential wall of the flexible tubular part. When an object, catheter or male Luer, is inserted through the traverse slit, the opposite two parts of the upright rib is pressed away from each other towards the circumferential wall of the flexible tubular part, both of which in combination then are pressed against the wall of the housing, hub, channel or passageway inside which the self-sealing catheter valve is mounted. Once the object is removed again the upright rib springs back to its starting position and then serves as a means for the self-sealing flexible diaphragm to reassume it's curved shape and thus a means to close the traverse slit fluid-tight.

The self-sealing proximal valve part may comprise an annular skirt or rim defining the base perimeter, which annular skirt or rim opposite the base perimeter extends into the curved self-sealing flexible diaphragm, in which embodiment the self-sealing flexible diaphragm can be substantially hemispherical or domed. The annular skirt preferably extends substantially parallel to the circumferential wall of the tubular part in the direction towards the distal opening, whereas a rim may be a bead that serves for direct and increased securing to the interior diameter of the circumferential wall of the tubular part. Optionally, the annular skirt or rim is defined by a length of the tubular part, thus being integral with the circumferential wall of the tubular part at the proximal valve part.

In both the above exemplary embodiments the curved self-sealing flexible diaphragm spans almost the entire diameter of the flexible tubular part so that this curved compression form in itself is sufficient to counteract the blood pressure. Forces acting on the opposite concave surface and convex surface are forces becoming resolved into compressive stresses and forces that eliminates tensile stresses on the self-sealing flexible diaphragm. The forces acting on the self-sealing flexible diaphragm due to the blood pressure or infusion liquid pressure are carried towards the base perimeter thereby making the base perimeter, and optionally the annular skirt, to be pushed outward towards the flexible tubular part, and thus pushed outward towards the catheter hub inside which the self-sealing catheter valve is positioned. This pressure on the convex surface and resulting "flattening" also moves the edges of the traverse slit towards each other to create the sealing properties.

The traverse slit may preferably extend at least 60% across the width or diameter of the curved self-sealing flexible diaphragm, preferably at least 70% to accommodate various inserted, circumferentially obturating, hollow or solid objects, such as a male Luer or a catheter, or a capping means or a plug, respectively.

The self-sealing flexible diaphragm curves inside the tubular part towards the distal opening so that a gap is defined, at least between the top of the convex surface of the flexible diaphragm and the interior surface of the circumferential wall of the flexible tubular part. Fluid pressures acting on the flexible diaphragm when no object is inserted distribute substantially equally over the entire curved area, thus also the areas closest to the tubular part, with total forces or a main force component in the direction normal to the convex surface, to induce closure of the traverse slit. A further advantage is that this gap confers resiliency to the flexible diaphragm when inserting the object through the traverse slit.

The upright rib may merge into the circumferential wall inside the flexible tubular part. Alternatively a clearance is left between the upright rib of said self-sealing flexible diaphragm and the interior surface of the circumferential wall of the flexible tubular part. In both embodiments lateral forces conferred to the traverse slit by an inserted object presses the split upright rib apart to be compressed towards the circumferential wall of the tubular part to a more or less degree. Once the object is removed compressive forces are released and the upright rib returns to its original shape to close the traverse slit. The tendency of the upright rib to return to its shape applies a sealing force on slit rims or slit edges that creates the superior sealing property, e.g. around an object, such as a catheter, being inserted in the traverse slit, including mounted in the traverse slit.

The exterior surface of the circumferential wall of the flexible tubular part may further have at least two protuberances positioned diametrical opposite each other on a line taken through the upright diametrical rib of the self-sealing flexible diaphragm. The at least two opposite protuberances, may optionally be placed on the exterior surface of the tubular part in alignment with the ends of the upright rib, to increase the closing pressure on the slit rims or slit edges when the self-sealing catheter valve is placed in a catheter hub. The protuberances may in some embodiments serve for providing a very small clearance between the circumferential wall of the tubular part and the circumferential wall of the catheter hub when inserted, to increase flexibility and facilitate inserting of the self-sealing catheter valve in the catheter hub. In other embodiments also the protuberances are compressed so that the tubular part is in full contact with the wall of the catheter hub as well.

The present invention thus provides a split self-sealing catheter valve having a curved self-sealing flexible diaphragm reinforced by an upright rib extending substantially perpendicular to the traverse slit. The upright rib acts as a "girder", e.g. of silicone, resulting in increased pressure to the opposite edges of the traverse slit. The upright rib also prevents sustained malformation of the traverse slit from the needle guidewire.

An annular flange at the proximal opening advantageously serves as a stop means to prevent axial displacement of the self-sealing catheter valve upon manipulation of the catheter, e.g. when passing parts of an over-the-needle-catheter in and out through the self-sealing flexible diaphragm, when inserting a male Luer through the traverse slit to establish infusion, and when removing same male Luer temporarily. For this purpose it is preferred that the exterior diameter of the annular flange is larger than the exterior diameter of the flexible tubular part so that the annular flange e.g. can fit into a complementary recess in the catheter hub, or the free end at the catheter hub opening may serve as an abutment face for the annular flange, or the flange simply helps to hold the flexible catheter valve in improved frictional engagement.

So the annular flange serves to keep the self-sealing catheter valve in position, especially when the male Luer is introduced. Moreover, in the conventional catheter assemblies, injection through the side injection port results in compression and displacement of a flexible tubular part to allow the infusion fluid to pass out through the catheter part into the blood vessel. However it is dependent on that the proximal part of the catheter assembly is closed by a cap, such as a Luer cap. Otherwise the infusion fluid will leak out of the proximal end of the catheter assembly. In the present invention no cap is essential since the proximal opening of the catheter assembly is sealed fluid tight by the self-sealing catheter valve. The annular flange keeps the self-sealing catheter valve in place in the catheter hub, and without the fixation resulting from the annular flange, the self-sealing catheter valve would be ejected out from the catheter hub when pressurized when injecting fluid into the blood vessel via the side injection port.

Anyone or both of the flexible tubular part and the self-sealing flexible diaphragm may have a circular or an oval interior cross-section and/or a circular or an oval exterior cross-section. If e.g. an embodiment of a self-sealing catheter valve wherein both the tubular part and the self-sealing flexible diaphragm have exterior oval cross-section is placed inside a catheter hub having circular interior cross-section the "oval self-sealing catheter valve" will assume circular cross-section and inherently be kept correctly positioned inside the catheter hub due to frictional forces between hub wall and the wall of the self-sealing catheter valve. The oval shape also is an additional means to force the slit edges to close fluid-tight around an inserted catheter and around a male Luer.

The length of the tubular part can preferably be selected to pass below an injection port of a peripheral catheter assembly or hub, such as a side injection port. Thus the centre axis of the injection port may traverse the longitudinal axis of the self-sealing catheter valve. Preferably the centre axis of the injection port traverses the longitudinal axis of the self-sealing catheter valve substantially perpendicularly.

So the exterior cross-section of the circumferential wall of the tubular part is selected so that this circumferential wall engages the interior wall of the passageway inside which the self-sealing catheter valve is mounted, normally the passageway is the passageway of a catheter hub.

The largest distance from the base perimeter to the bottom of the concave surface of the curved self-sealing flexible diaphragm may be less than or equal to 25% of the total distance between the base perimeter and the distal opening, alternatively less than or equal to 20%, alternatively less than or equal to about 17%, to ensure that the proximal valve part does not reach below the injection port of the self-sealing catheter valve.

In a preferred embodiment the depth of the curved self-sealing flexible diaphragm is substantially equal to the axial distance of the annular skirt, optionally the depth of the curved self-sealing flexible diaphragm is about 5% larger than the axial distance of the annular skirt.

In a particular efficient embodiment the entire proximal valve part is accommodated inside the flexible tubular part so that the proximal end of the tubular part, and thus the proximal opening, is easy accessible and provides expedient guidance for inserting an object through the traverse slit. The distal end of the flexible tubular part is so long that it can pass below the injection port to function as yet a valve that closes the injection port when the injection port is left un-operated. The circumferential wall of the distal part of the flexible tubular part yields in response to pressure applied during injection through the injection port, and reassumes its in-build shape to again cover and close the injection port at the transition opening to the hub once injection pressure stops.

The wall thickness of the circumferential wall of the flexible tubular part may decrease towards the distal opening to provide any or both of a minimal tapering that facilitates guided mounting in the catheter hub, and/or a larger diameter for fluid flow at the distal opening than at the diameter of the flexible tubular part around the curved self-sealing flexible diaphragm.

The catheter valve of the present invention is configured to open in response to inserting an object along the longitudinal axis of the self-sealing catheter valve and to close automatically when the object is removed.

The catheter valve is in particular advantageously in a intraveneous catheter assembly, wherein its operation is performed without any manual application of force crosswise the valve to open and close it. The only thing that can open the catheter valve is the inserted object.

The invention also relates to a peripheral catheter assembly comprising the self-sealing catheter valve discussed and described above.

BRIEF DESCRIPTION OF THE DRAWINGS

The invention will be described below in further details with reference to the drawing in which.

DETAILED DESCRIPTION OF THE INVENTION

Figures 1, 2, 3:
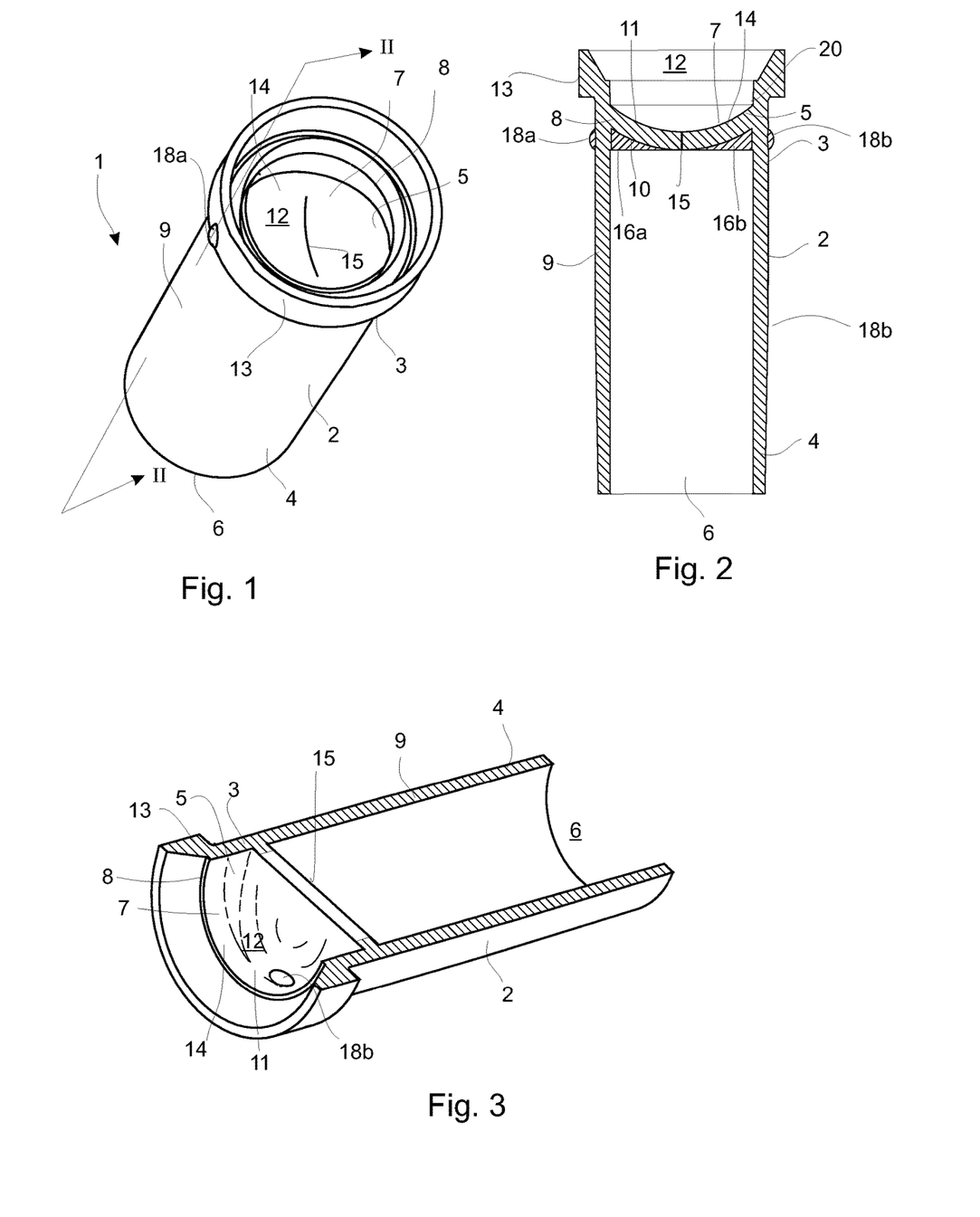
FIG. 1 is a perspective view of a first embodiment of a self-sealing catheter valve seen oblique from the proximal end.
FIG. 2 is a sectional view taken along line II-II of FIG. 1.
FIG. 3 shows, in perspective, half of a self-sealing catheter valve, obtained by an axial cut through the traverse slit.

FIG. 1 is a perspective view of a first embodiment of a self-sealing catheter valve 1 according to the present invention. The self-sealing catheter valve 1 has a flexible tubular part 2 with a proximal end part 3 that extends into a distal end part 4. A proximal valve part 5 is arranged inside the flexible tubular part 2 closer to the proximal end part 3 than to the distal end part 4, thereby enabling at least the distal end part 4 to pass below an injection port (not shown) of a catheter hub (not shown) to also serve as an injection valve 4 for the injection port.

The distal end part 4 of the flexible tubular part 2 has a distal opening 6 through which infusion liquid can pass further into the catheter and the blood vessel, and via which distal opening 6 back flow of blood via the inserted catheter can enter the self-sealing catheter valve 1 to reach the proximal valve part 5.

The proximal valve part 5 has a curved self-sealing flexible diaphragm 7 disposed inside the flexible tubular part 2. The proximal valve part 5 has a base perimeter 8 united with a circumferential wall 9 of the flexible tubular part 2 so that the curved self-sealing flexible diaphragm 7 protrudes towards the distal opening 6.

The curved self-sealing flexible diaphragm 7 has a concave surface 11 facing towards the proximal opening 12, and a convex surface 10 facing towards the opposite distal opening 6 of the distal end part 4. The proximal end part 3 has a flange 13 terminating the proximal opening 12. The wall 14 of the curved self-sealing flexible diaphragm 7 of the proximal valve part 5 has a traverse slit 15 to allow passage of objects such as an inserted catheter or a male Luer (not shown), around which the traverse slit 15 conforms to seal tightly. A short annular skirt 20 is provided as a short length of circumferential wall of the proximal end part 3 and extends into the flange 13.

An upright rib 16 is provided on the convex surface 10 of the wall 14 of the curved self-sealing flexible diaphragm 7. The upright rib 16 is arranged substantially perpendicular to the traverse slit 15 so as to divide the traverse slit 15 into two opposite upright flexible fins 16a,16b. The ends 17a,17b of the fins 16a,16b may be joined to the circumferential wall 9 of the flexible tubular part 2 or be free to flex in engagement with the circumferential wall 9 of the flexible tubular part 2. Two opposite protuberances 18a,18b or beads are provided aligned with the ends of the upright rib 16 on the exterior surface of the circumferential wall 9 of the flexible tubular part 2. When an object is inserted in the traverse slit 15 it presses the ends of the two opposite upright flexible fins 16a,16b against the flexible tubular wall 2 and thus also on the respective protuberances 18a,18b, to engage the rigid wall of a catheter hub wherein the self-sealing catheter valve 1 is inserted. This way is created compressive forces that make the traverse slit 15 to close and seal tightly around the object, and so that when the object is removed the traverse slit 15 automatically closes, simply by virtue of releasing compressive forces and tension previously provided to the proximal valve part 5 by the inserted object.

Figure 4:
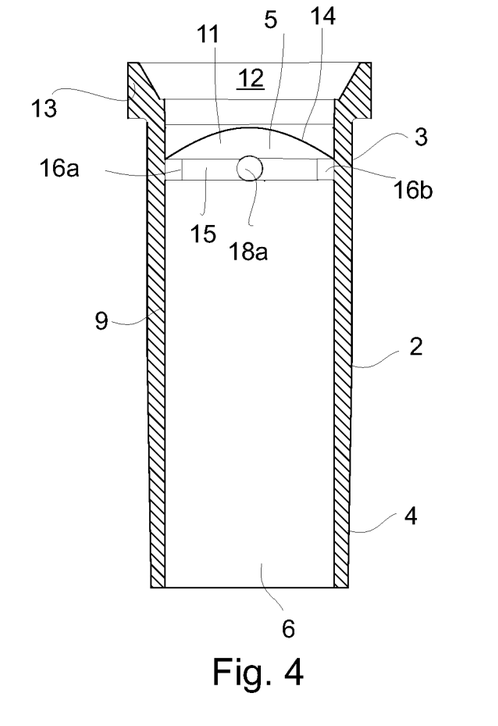
FIG. 4 is a sectional axial view taken in a plane through the traverse slit.

FIG. 4 is a sectional axial view of FIG. 1 taken in a plane through the traverse slit 15 to illustrate the curvature of the curved self-sealing flexible diaphragm 7. The base perimeter 8 is seen joined to the circumferential wall 9 of the flexible tubular part 2.

Figure 5:
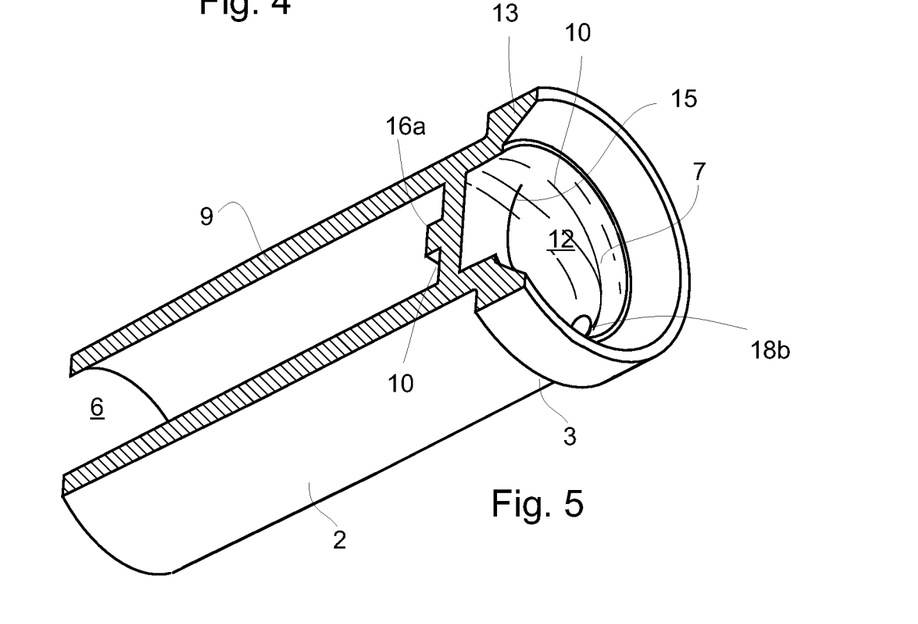
FIG. 5 shows, similar to FIG. 3, the self-sealing catheter valve but intersected along an axial sectional line offset towards the circumferential wall of the tubular part.

FIG. 5 shows, similar to FIG. 3, the self-sealing catheter valve 1 intersected along a sectional line offset towards the circumferential wall 9 of the flexible tubular part 2 to illustrate that that the curved self-sealing flexible diaphragm 7 has a certain thickness, e.g. similar to the thickness of the circumferential wall 9 of the proximal end part 3 of the flexible tubular part 2, or slightly thicker, and that the upright fins 16a,16b merge into the curvature of the convex surface 10 of the curved self-sealing flexible diaphragm 7 in front of respective protuberances 18a,18b.

Figure 6:
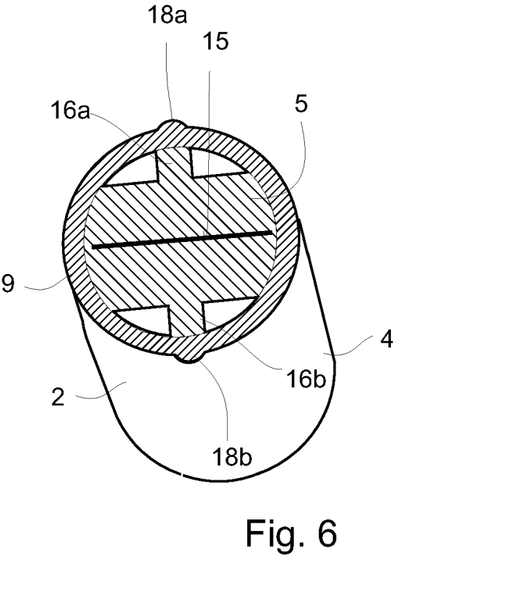
FIG. 6 shows a cross-section taken through the plane of the protuberances.

FIG. 6 shows a cross-section taken through the plane of the protuberances, and thus also through the top of the convex surface 10.

Figure 7:
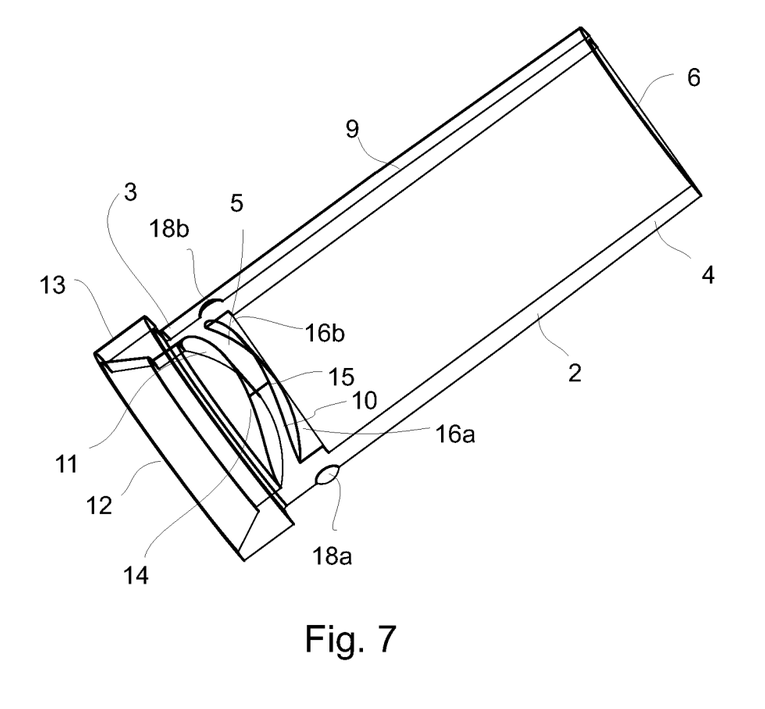
FIG. 7 is a transparent view of the self-sealing catheter valve seen in FIG. 1 oblique from the side.

FIG. 7 is a transparent view of the self-sealing catheter valve to visualize the curvature of the curved self-sealing flexible diaphragm 7 and it's attachment inside the flexible tubular part 2. FIG. 7 otherwise corresponds to FIG. 1.

Figure 8:
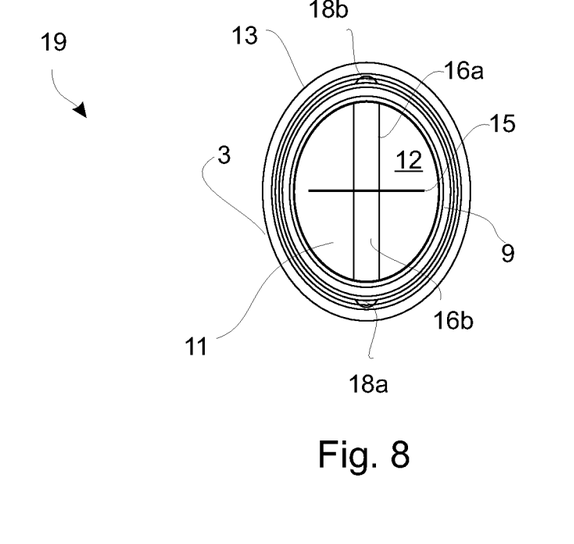
FIG. 8 shows a second embodiment of a self-sealing catheter valve seen from the proximal opening.

FIG. 8 shows a second embodiment of a self-sealing catheter valve 19 seen from the proximal opening 12. The second embodiment 19 only differs from the first embodiment 1 in that the cross-section is oblong instead of substantially circular, so for like parts same reference numerals are used. Thus the second embodiment of a self-sealing catheter valve 19 has a major diameter greater than the minor diameter.

When the second embodiment 19 is inserted in a catheter hub having a circular cross-section the mismatch between respective cross-sections forces the self-sealing catheter valve 19 to conform to circular tubular shape, thereby obtaining an inherent frictional engagement that, on the one hand prevents dislocation upon manipulation of the catheter, and on the other hand, since the major diameter of the oblong cross-section is greater than the internal diameter of the catheter hub, keeps and forces the edges of the traverse slit 15 tight together as a result of the pressure exerted on the protuberances and the upright rib by the catheter hub wall.

For arrangement and positioning of the self-sealing catheter valve 1,19 according to the present invention in a catheter hub, references are made to applicant's international patent application no. WO 2009 016184, which arrangement, positioning and catheter assembly are incorporated by reference in the present application.

Comparative catheter valves are shown in the followings FIGS. 9a,9a,9b,10a,10b,10c,11a,11b. These catheter valves differ from the valves 1,19 of the present invention in having different proximal valve parts.

Figure 9A:
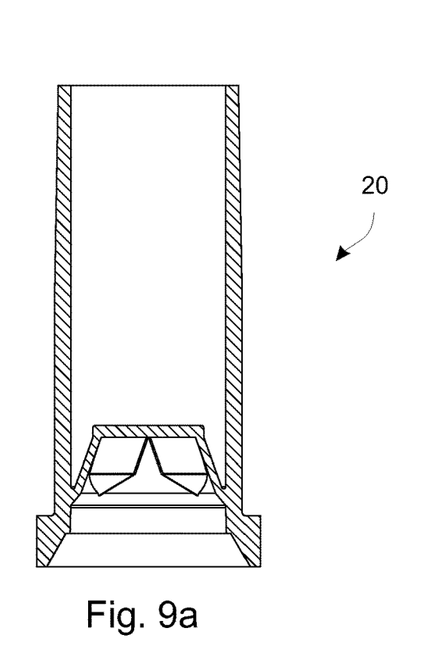
FIG. 9a shows a longitudinal sectional view of a catheter valve including a flexible tubular part and a proximal valve part in form of a conventional cross slit valve.
Figure 9B:
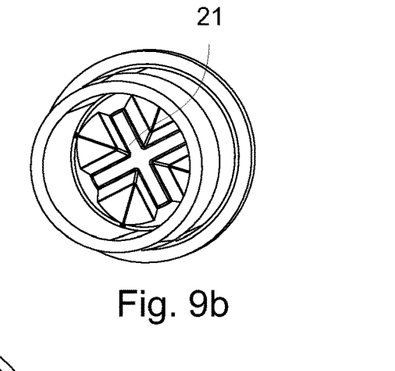
FIG. 9b shows, in perspective from the proximal end obliquely inside the catheter valve of FIG. 9a, the proximal valve part of said catheter valve.
Figure 9C:
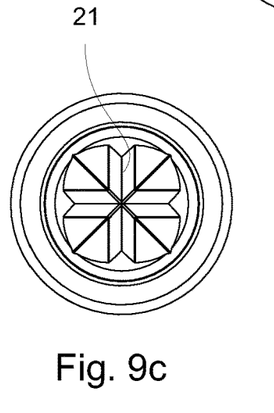
FIG. 9c shows the catheter valve seen in FIG. 9a from the distal end.

The comparative catheter valve 20 seen in FIGS. 9a,9b,9c has a proximal valve part in form of a conventional cross-slit valve 21.

Figure 10A:
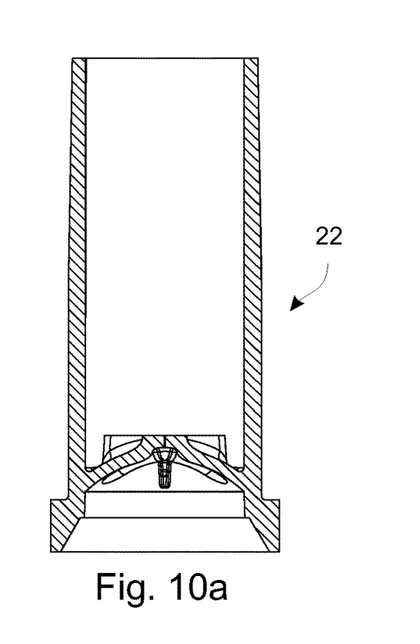
FIG. 10a shows a longitudinal sectional view of a catheter valve including a flexible tubular part and a proximal valve part in form of a conventional multi-slotted dome valve.
Figure 10B:
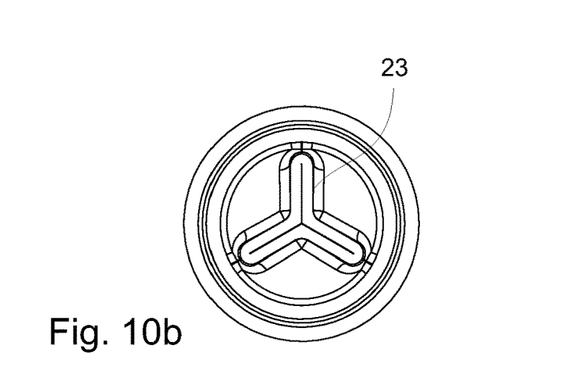
FIG. 10b shows the catheter valve of FIG. 10a from the proximal end.
Figure 10C:
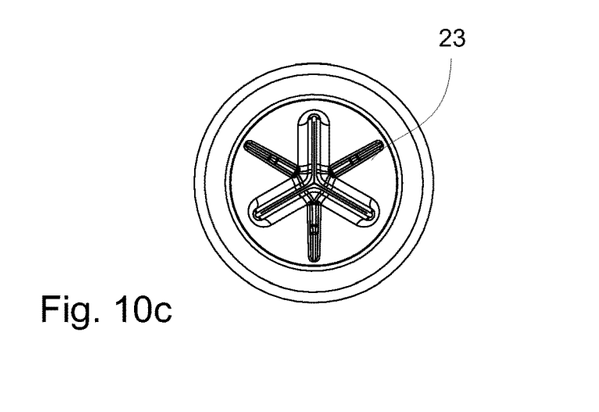
FIG. 10c shows the catheter valve seen in FIG. 10a from the distal end.

The comparative catheter valve 22 seen in FIGS. 10a, 10b,10c has a proximal valve part in form of a conventional multi-slotted dome valve 23.

Figure 11A:
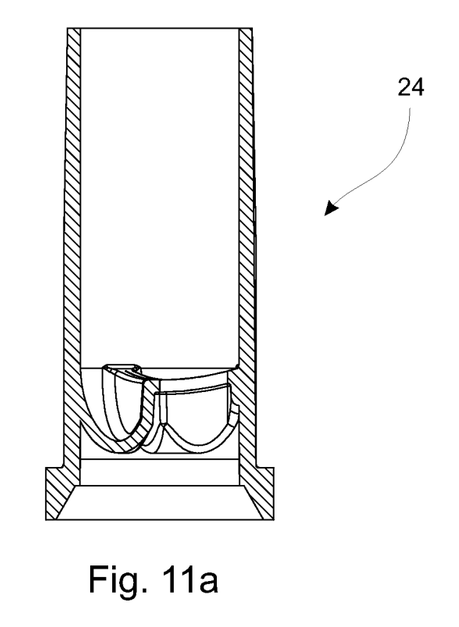
FIG. 11a shows a longitudinal sectional, perspective, view of a catheter valve including a flexible tubular part and a proximal valve part in form of a conventional aortic valve shape.
Figure 11B:
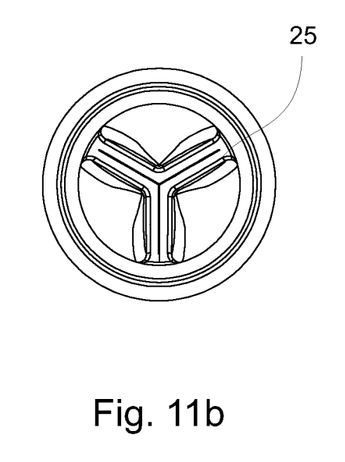
FIG. 11b shows the catheter valve seen in FIG. 11a from the distal end.

The comparative catheter valve 24 seen in FIGS. 11a,11b has a proximal valve part in form of a conventional aortic valve shape.

Comparison Example

Catheter valves having flexible tubular parts and different conventional proximal valve parts were produced, compared and tested under various conditions on different subjects following the below valve testing protocol:
  In vitro short-term
    Fluid pressure 30 mmHg
  In vitro long-term, after 6 month storage
    Fluid pressure 30 mmHg
  In vitro after gamma-sterilization
    Fluid pressure 30 mm Hg
  Animal test in pigs, n=10
    Blood pressure 70 mmHg
  Human evaluation, sterilized product, n=10
    Venous blood pressure 50 mmHg The results of the tests are shown in the Table below, where also a simple split septum valve, such as a split septum valve described in WO 2009 016184, applied in a flexible tubular part were subjected to tests.

| Valve design | Lab test short term, n = 20, % leakage | Lab test long term, n = 20, % leakage | Lab test after sterilization, n = 20, % leakage | Animal test pigs n = 10, % leakage | Human, sterile n = 10, % leakage |
|---|---|---|---|---|---|
| Split Septum (not shown) | 80% | 100% | | | |
| Cross slit valve (FIGS. 9a, 9b9c) | 10% | 15% | | 15% | |
| 3D-dome valve (FIGS. 10a, 10b, 10c) | 0% | 10% | 10% | 15% | 30% |
| Aortic valve shape (FIGS. 11a, 11b) | 15% | 30% | | | |
| Self-sealing valve (invention) | 0% | 0% | 0% | 0% | 0% |

The comparative study reveals the superior sealing properties of the self-sealing catheter valve according to the present invention in that under all test conditions and in all test environments no leakage was seen.

Preferred polymeric materials for manufacturing the self-sealing catheter valve according to the present invention include but is not limited to the liquid silicone rubbers of the SILPURAN® 6600 series obtainable from Wacker Chemie AG, Hans-Seidel-Platz 4, 81737 Munchen, Germany, e.g. SILPURAN® 6600/50 A/B.

The self-sealing catheter valve according to the present invention provides an efficient self-closing mechanism for a peripheral catheter assembly and constitutes an efficient barrier against potential contagious spread from the patient to the surrounding environment by blood born disease e.g. HIV, hepatitis and Ebola viruses.

Furthermore, the self-sealing catheter valve according to the present invention makes venipuncture must easier than hitherto known, providing the physician with a freedom to leave the patient after puncture. No blood flows unintended out of the peripheral catheter when no male part is inserted through the traverse slit and nothing enters inside the blood stream since the catheter hub always is either sealed or plugged.

The self-sealing catheter valve according to the present inventions provides an optimum protection of personal from blood spillage and blood born contamination from the patient.

So the combination of the flexible tubular part sealing the injection port and the design of the curved self-sealing flexible diaphragm preventing blood leakage when the catheter is positioned in the pressurized blood vessel is unique to the present invention. Previous designs with a simple split septum or valve constructions, such as duck-bill valve or other valve constructions, have suffered from defects in the coaptation of the split septum rims or valve edges due to malformation of these parts from the steel needle positioned over time and after sterilization procedure.

What is claimed is:

1. A peripheral catheter assembly comprising:
  a catheter hub or other tubular passageway that has an internal surface; and
  a self-sealing peripheral catheter valve including:
    a flexible tubular part having a distal opening and an opposite proximal opening, and
    a proximal valve part that has a curved self-sealing flexible diaphragm disposed inside the flexible tubular part and has a base perimeter united with a circumferential wall of the flexible tubular part at an axial distance from the proximal opening of said catheter valve, and an annular flange which defines or includes the base perimeter and which has an external surface that includes an exterior diameter that is larger than the exterior diameter of the flexible tubular part, wherein the curved self-sealing flexible diaphragm has a concave surface facing towards the proximal opening and a convex surface facing towards the distal opening, and wherein the curved self-sealing flexible diaphragm has a traverse slit, wherein the convex surface of the curved self-sealing flexible diaphragm has an upright rib extending crosswise and perpendicular to the traverse slit towards the interior surface of the circumferential wall of the flexible tubular part, and wherein the catheter valve is present in the catheter hub or passageway with the external surface of the annular flange of the tubular part in contact with the internal surface of the catheter hub or passageway, so that the catheter valve provides a fluid tight seal in the catheter hub or passageway, wherein the exterior surface of the circumferential wall of the flexible tubular part has at least two protuberances, positioned diametrically opposite each other on a line taken through the upright diametrical ribs of the diaphragm.

2. The self-sealing peripheral catheter valve according to claim 1, wherein the proximal valve part comprises an annular skirt or rim defining or including the base perimeter, which annular skirt or rim opposite the base perimeter extends into the curved self-sealing flexible diaphragm, optionally wherein the annular skirt or rim is defined by a length of the flexible tubular part, and further optionally the rim is the base perimeter.

3. The self-sealing peripheral catheter valve according to claim 1, wherein the traverse slit extends at least 60% or at least 70% across and through the center of the curved self-sealing flexible diaphragm.

4. The self-sealing peripheral catheter valve according to claim 1, wherein the upright rib merges into the circumferential wall of the flexible tubular part inside said flexible tubular part, or a clearance is delimited between the upright rib of the self-sealing flexible diaphragm and the interior surface of the circumferential wall of the flexible tubular part.

5. The self-sealing peripheral catheter valve according to claim 1, wherein one or both of the flexible tubular part and the curved self-sealing flexible diaphragm has a circular, oblong, or oval interior cross-section, and/or a circular, oblong or oval exterior cross-section.

6. The self-sealing peripheral catheter valve according to claim 1, wherein the flexible tubular part has one or more of:
a length selected to pass below an injection port of a peripheral catheter assembly or hub, wherein the center axis of the injection port traverses the longitudinal axis of the self-sealing peripheral catheter valve, optionally with the center axis of the injection port traversing the longitudinal axis of the self-sealing peripheral catheter valve substantially perpendicularly, or
a cross-section selected so that the circumferential wall engages the channel inside which the self-sealing peripheral catheter valve is mounted.

7. The self-sealing peripheral catheter valve according to claim 1, wherein the largest distance from the base perimeter to the bottom of the concave surface of the curved self-sealing flexible diaphragm is less than or equal to 25%, less than or equal to 20% or less than or equal to 17% of the total distance between the base perimeter and the distal opening.

8. The self-sealing peripheral catheter valve according to claim 2, wherein the depth of the curved self-sealing flexible diaphragm is equal to or about 5% larger than the axial distance of the annular skirt or rim.

9. The self-sealing peripheral catheter valve according to claim 1, wherein the entire proximal valve part is accommodated inside the flexible tubular part.

10. The self-sealing peripheral catheter valve according to claim 1, wherein the wall thickness of the circumferential wall of the flexible tubular part decreases towards the distal opening.

11. The self-sealing peripheral catheter valve according to claim 1, which is configured to open in response to inserting an object along the longitudinal axis of the self-sealing peripheral catheter valve and to close automatically when the object is removed.

12. The self-sealing peripheral catheter valve according to claim 1, wherein the upright rib extends transversely from the traverse slit towards the interior surface of the circumferential wall of the flexible tubular part.

13. The self-sealing peripheral catheter valve according to claim 1, wherein the upright rib is adapted to be pressed on the protuberance to engage with the internal surface of the catheter hub or passageway.

14. A self-sealing peripheral catheter valve comprising:
a flexible tubular part having a distal opening and an opposite proximal opening, and a circumferential wall having an exterior surface, and
a proximal valve part that has a curved self-sealing flexible diaphragm disposed inside the flexible tubular part and has a base perimeter united with a circumferential wall of the flexible tubular part at an axial distance from the proximal opening of said catheter valve, and an annular flange which defines or includes the base perimeter and which has an external surface that includes an exterior diameter that is larger than the exterior diameter of the flexible tubular part,
wherein the curved self-sealing flexible diaphragm has a concave surface facing towards the proximal opening and a convex surface facing towards the distal opening, and
wherein the curved self-sealing flexible diaphragm has a traverse slit extending at least 70% across and through the center of the curved self-sealing flexible diaphragm,
wherein the convex surface of the curved self-sealing flexible diaphragm has a supporting rib on each side of the transverse slit, wherein the ribs extending crosswise and perpendicular to the slit, have an upper surface that conforms to the convex surface of the diaphragm and a lower linear surface facing the interior surface of the flexible tubular part, and
wherein the exterior surface of the circumferential wall of the flexible tubular part has at least two protuberances, positioned diametrically opposite each other on a line taken through the upright diametrical ribs of the diaphragm.

15. A peripheral catheter assembly comprising the self-sealing peripheral catheter valve according to claim 14, wherein the catheter has a catheter hub that has an internal surface, and wherein the catheter valve is present in the catheter hub with the external surface of the annular flange of the tubular part in contact with the internal surface of the catheter hub so that the catheter valve provides a fluid tight seal in the catheter hub.

* * * * *